US006935198B2

(12) United States Patent
Jaeger

(10) Patent No.: US 6,935,198 B2
(45) Date of Patent: Aug. 30, 2005

(54) SAMPLING APPARATUS HAVING A LINEAR INDEXING SAMPLE COLLECTION STATION

(76) Inventor: Ben E. Jaeger, 50 Hunter La., Bristol, IL (US) 60512

( * ) Notice: Subject to any disclaimer, the term of this patent is extended or adjusted under 35 U.S.C. 154(b) by 278 days.

(21) Appl. No.: 10/427,761

(22) Filed: Apr. 30, 2003

(65) Prior Publication Data

US 2004/0237672 A1 Dec. 2, 2004

(51) Int. Cl.$^7$ ................................................ G01N 1/00
(52) U.S. Cl. .................................................... 73/864.31
(58) Field of Search ........................ 73/863.01, 863.31, 73/863.52, 863.53, 863.83, 864, 864.31, 864.32, 864.34, 864.51, 864.63; 141/130, 163, 135

(56) References Cited

U.S. PATENT DOCUMENTS

| | | | |
|---|---|---|---|
| 4,147,062 A | | 4/1979 | Jaeger |
| 4,262,533 A | | 4/1981 | Jaeger |
| 4,475,410 A | | 10/1984 | Jaeger |
| 4,718,288 A | * | 1/1988 | Leschonski et al. .......... 73/863 |
| 4,744,255 A | | 5/1988 | Jaeger |
| 4,869,117 A | * | 9/1989 | McAndless et al. ..... 73/864.34 |
| 5,553,508 A | * | 9/1996 | Dabberdt et al. ........ 73/863.02 |
| 6,152,189 A | * | 11/2000 | Wright et al. .................. 141/2 |

* cited by examiner

*Primary Examiner*—Robert Raevis
(74) *Attorney, Agent, or Firm*—Pyle & Piontek

(57) ABSTRACT

A sampling apparatus is characterized by a sampler and a sample collection station. The sampler is stationary and periodically delivers discrete product samples to a stationary inlet to the sample collection station. The sample collection station includes a deck having a plurality of passages in linearly aligned spaced relationship, a plurality of sample collection containers, and inlets to the sample collection containers that are in communication with associated ones of the deck passages. The deck is linearly indexed in both directions of movement along the linear alignment of the deck passages to place selected ones of the deck passages into communication with the stationary inlet, so that product samples delivered by the sampler to the sample collection station are directed into selected ones of the sample collection containers. The use of a plurality of sample collection containers at the sample collection station provides an increased product sample collection capacity and extends the time for which product samples may be collected before the station reaches its capacity and requires operator attendance to replace full with empty sample collection containers. A generally side-by-side alignment of the sample collection containers provides an unobstructed view of the containers to allow all of the containers to be simultaneously visually inspected by an operator.

20 Claims, 6 Drawing Sheets

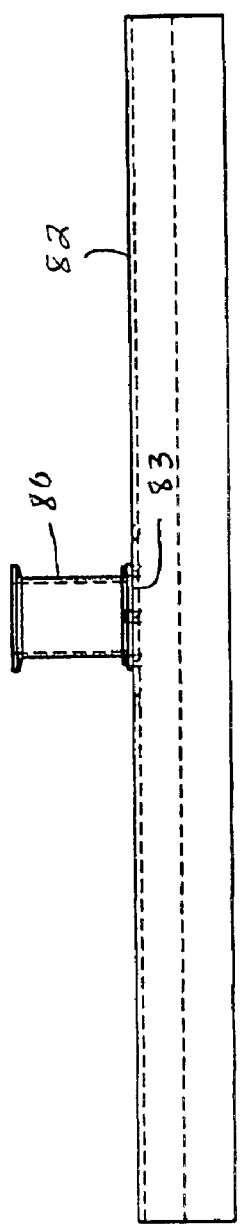
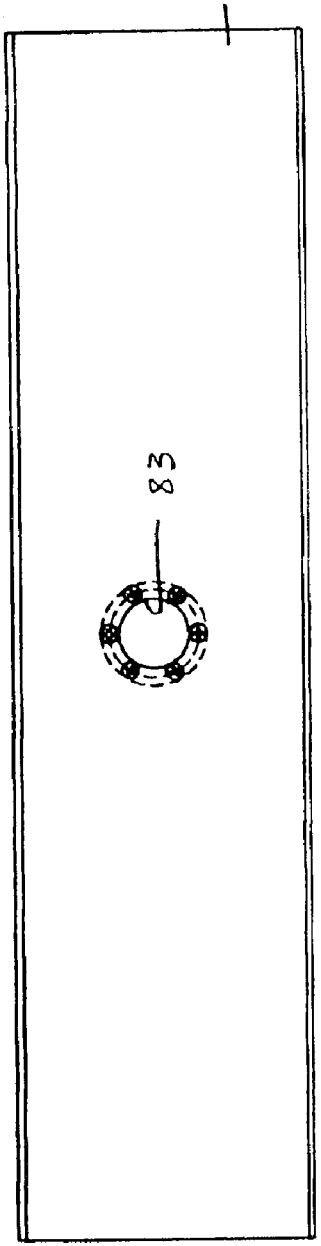
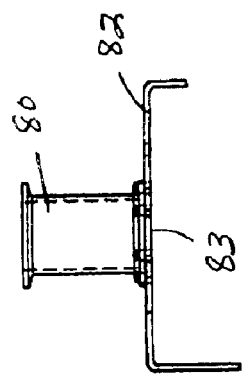
FIG. 6A
FIG. 6B
FIG. 6C

SAMPLING APPARATUS HAVING A LINEAR INDEXING SAMPLE COLLECTION STATION

BACKGROUND OF THE INVENTION

The present invention relates to product sampling apparatus, and in particular to sampling apparatus in which extracted samples are directed to selected ones of a plurality of sample collection containers.

Certain product manufacturing operations require that the composition of the product be monitored to obtain representations of what is being generated by the manufacturing process. Monitoring may be accomplished with samplers that take samples of product from a main body of the product. When a composite sample is required, the sampler may be periodically operated over time to withdraw and collect a plurality of discrete samples of product from the main body, which samples are mixed together and represent a composite of the product. If the immediate composition of a product is to be determined, the samples are individually analyzed.

Four exemplary types of known sampling apparatus are disclosed in U.S. Pat. Nos. 4,147,062, 4,262,553, 4,475,410 and 4,744,255, issued to Ben E. Jaeger, the present inventor, and the teachings of all of which are incorporated herein by reference. Samplers of the type disclosed in said patents are attached about an opening to a pipe or vessel that contains product to be sampled. The samplers have a plunger in which is a sample receiving recess, and the plunger and recess are extended through the opening to the vessel to project the recess into the main body of product in the vessel to receive a product sample in the recess. The plunger and its product sample containing recess are then retracted to deliver the product sample to a collection point in the sampler.

When a sampler is operated to obtain discrete product samples and deliver the samples to a collection point, a sample collection container normally is provided at the collection point to receive and hold the samples. Sample collection containers are of limited size and can hold only a finite number of product samples before becoming full, so it is necessary that the sample collection container be attended to from time to time in order to replace full sample collection containers with empty containers. The time interval between replacements depends upon the capacity of the containers, the product sample rate and the volumetric size of the discrete samples delivered to the containers. When the interval is relatively short, replacement of full with empty sample collection containers can be inconvenient, time consuming, require the presence of a person who might be otherwise gainfully occupied, and add unwanted costs to the sampling operation.

Prior efforts to alleviate the problem of having to frequently replace full with empty sample collection containers contemplate using rotary indexing samplers, in which a turntable carries a plurality of sample collection containers in an arcuately spaced circular array. The turntable is rotated to place selected ones of the collection containers in position to receive samples delivered by a sampler, with the use of a plurality of collection containers serving to increase the capacity of the sample collection station and extend the time interval between the need to replace of full with empty containers. A disadvantage to rotary indexing samplers is that because the plurality of collection containers are arranged in a circular array, an operator observing the sample collection station has his view of the remote collection containers obstructed by the near collection containers, much as a person standing alongside a merry-go-round has his view of the far horses blocked by the near horses. In consequence, an operator is not able to readily visually discern whether the remote collection containers are full and require replacement, or if samples delivered to the remote containers have encountered a blockage in the delivery line.

OBJECTS OF THE INVENTION

An object of the present invention is to provide a sampling apparatus in which the time intervals between replacements of full sample containers with empty sample containers is extended.

Another object is to provide such a sampling apparatus in which a plurality of sample collection containers have inlets in linearly spaced relationship and in which the inlets are linearly indexed to move selected ones of the inlets into position to receive product samples delivered by a sampler.

A further object is to provide such a sampling apparatus in which the sampler remains stationary while the inlets to the sample collection container are linearly indexed.

Yet another object is to provide such a sampling apparatus in which the sample collection containers are generally in side-by-side relationship, so that an operator visually inspecting the sampling apparatus may simultaneously view all of the collection containers.

SUMMARY OF THE INVENTION

In accordance with the present invention, a sampling apparatus comprises a sample collection station having a stationary inlet for receiving discrete samples, a plurality of sample collection containers, and of inlets to said sample collection containers, said inlets being in linearly aligned spaced relationship. Also included is means for indexing the inlets to the sample collection containers in both directions along the linear alignment of the inlets to move selected ones of the inlets into communication with the stationary inlet, so that discrete samples received at the stationary inlet are directed into selected ones of the sample collection containers.

The sample collection station includes a deck having passages therethrough in linearly aligned spaced relationship. The inlets to the sample collection containers are in communication with associated ones of the deck passages, and the means for indexing moves the deck to move the deck passages in both directions along the linear alignment of the deck passages to place selected ones of the deck passages into communication with the stationary inlet. In this manner, discrete samples received at the stationary inlet are directed through selected ones of the deck passages into associated ones of the sample collection containers.

The inlets to the sample collection containers may comprise openings to the sample collection containers. It is also contemplated that the inlets to the sample collection containers may include a plurality of movable spouts carried by the deck and having inlets in communication with associated ones of the deck passages and outlets in communication with associated ones of the sample collection containers, so that samples received at the stationary inlet are delivered through selected ones of the deck passages and associated spouts into associated sample collection containers.

In the described embodiment, the means for indexing comprises pneumatic motor means that includes a plurality of pneumatic cylinders, each having a cylinder and a piston rod and each being actuable between a first state where its piston rod is extended from its cylinder and a second state where its piston rod is retracted into its cylinder. Each pneumatic cylinder has a longitudinal axis extending along a longitudinal axis of its piston rod, and the plurality of pneumatic cylinders are connected in series along their longitudinal axes. The plurality of series connected pneumatic cylinders are coupled to the deck, and the pneumatic cylinders are individually selectively actuable between their first and second states to linearly move the deck in both directions along the linear alignment of the deck passages to position selected ones of the deck passages into communication with the stationary inlet.

To provide samples to the sample collection station, the sampling apparatus includes a sampler for obtaining discrete samples and for delivering the samples to the sample collection station stationary inlet. The sampler may be vertically above the sample collection station, and a conduit is coupled between an outlet from the sampler and the stationary inlet for conveying samples from the sampler outlet to the stationary inlet. The sampler may be coupled to a vessel that contains product to be sampled, and the sampler includes a plunger having a sample receiving recess that is extendable through an opening to the vessel into the product in the vessel to receive in the plunger recess a sample of product. The plunger and its sample containing recess are then retractable from the vessel into a body of the sampler to deliver the product sample in the recess to the sampler outlet. At the sampler outlet, the product sample moves from the plunger recess and through the sampler outlet into the conduit for being conveyed to the stationary inlet of the sample collection station.

The invention also provides a method of sampling product, which comprises the steps of obtaining discrete samples of product, conveying the discrete samples of product to a stationary sample receiving inlet, and providing a plurality of sample collection containers. Also included are the steps of providing a corresponding plurality of inlets to the sample collection containers, linearly aligning the inlets in spaced relationship, and indexing the inlets in both directions along the linear alignment of the inlets to place selected ones of the inlets into communication with the stationary inlet, so that discrete product samples conveyed to the stationary inlet are directed into selected ones of the sample collection containers.

The foregoing and other objects, advantages and features of the invention will become apparent upon a consideration of the following detailed description, when taken in conjunction with the accompanying drawings.

BRIEF DESCRIPTION OF THE DRAWINGS

FIGS. 6A is a front elevation view of a cover assembly of the sample collection station;

FIG. 6B is a bottom view of the cover assembly;

FIG. 6C is a side elevation view of the cover assembly;

DETAILED DESCRIPTION

The invention provides a sampling apparatus for use in applications in which a plurality of discrete product samples is to be collected for later analysis. The sampling apparatus is particularly adapted for use in situations where it is desirable to extend the time during which samples may be collected before it becomes necessary to attend the apparatus to replace filled with empty sample containers. This is accomplished by providing a plurality of sample collection containers at a sample collection station, and by also providing the sample collection station with means for periodically placing selected ones of the containers into position to receive product samples delivered from a sampler. Normally, a selected sample collection container will receive product samples delivered from the sampler for a given period, whereupon the sample collection station will be operated to place a different selected one of the collection containers into position to receive product samples. For example, in the embodiment described there are four sample collection containers at a sample collection station, so for an 8 hour sampling period, each container can be positioned to receive product samples for 2 hours. Having a plurality of sample collection containers, instead of just one, eliminates the need for a person to attend the sampling apparatus as often as might otherwise be required in order to replace filled with empty collection containers. Having multiple sample collection containers, each utilized for a given period, also allows a determination of how the composition of a sampled product changes over time.

Figure 1:
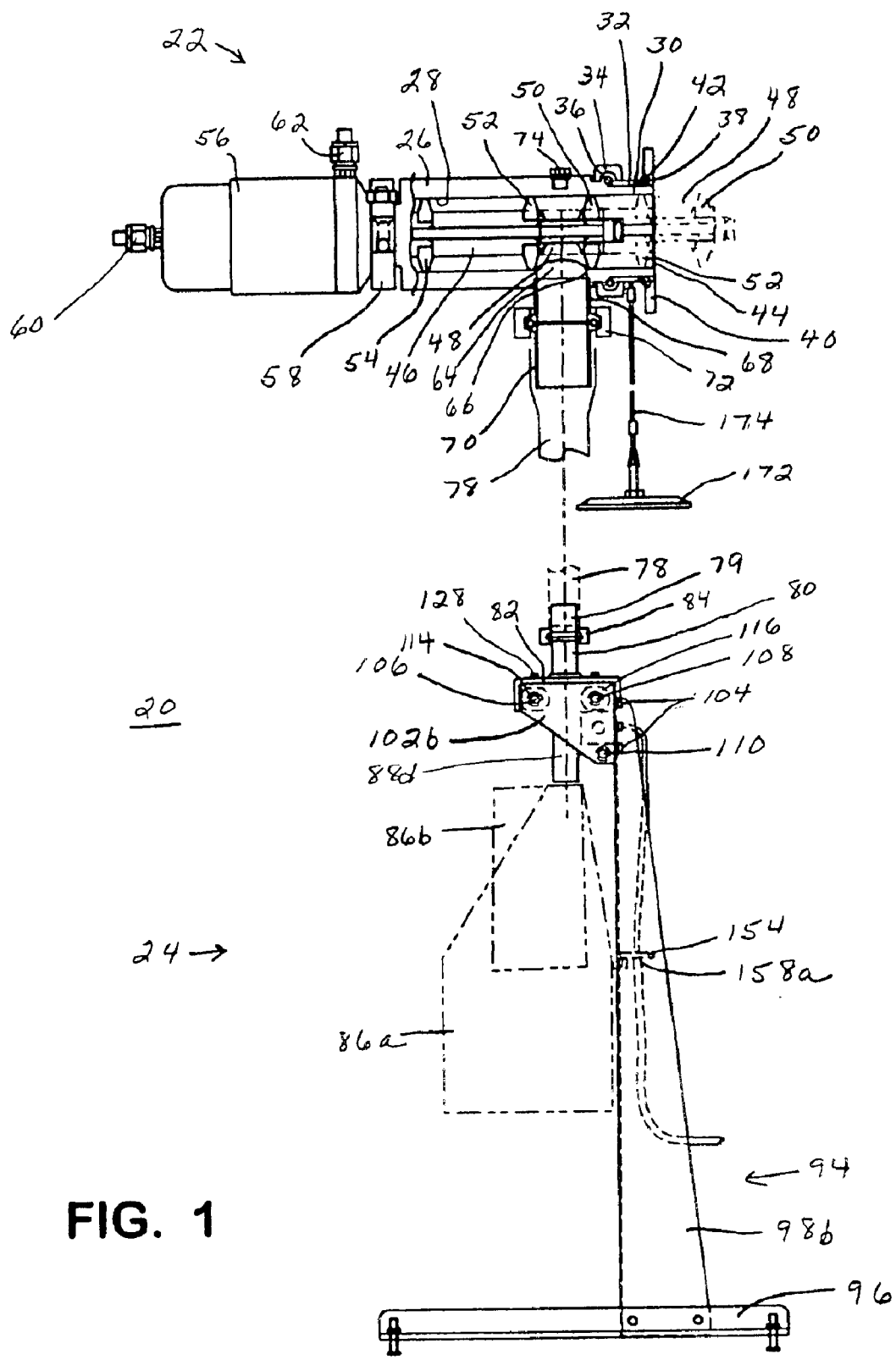
FIG. 1 is a side elevation view, showing a sampler for obtaining product samples from a main body of product and for delivering the samples to selected ones of a plurality of sample collection containers at a sample collection station.

Referring to FIG. 1, sampling apparatus according to the invention is indicated generally at 20 and includes a sampler and a sample collection station, respectively indicated at 22 and 24. The sampler 22 may be of the general type disclosed in U.S. Pat. Nos. 4,147,062, 4,262,553, 4,475,410 and 4,744,255, the teachings of all of which have been incorporated by reference. The sampler has a housing 26, a bore 28 extends through the housing and a forward cylindrical end 30 of the housing is received within a cylindrical adapter 32. The housing is attached to the adapter by a quick release clamp 34 and is sealed to the adapter by an annular seal 36. A forward end of the adapter is received in an opening 38 to a product containing vessel, tank or pipe 40, and the adapter is attached to the vessel by a circumferential weld 42. The adapter supports the sampler housing with an open forward end 44 of the housing bore communicating with the interior of the vessel and product therein, which may be dry material product, such as cocoa powder.

A plunger 46 in the sampler housing bore 28 has an annular recess 48 of predetermined volume intermediate its ends. The plunger carries an annular seal 50 at a forward end of the recess, an annular seal 52 at a rearward end of the recess, and an annular seal 54 toward its rearward end, all of which make sliding sealed contact with the housing 26 within the bore 28. A motor means, which as shown is a pneumatic cylinder 56, but could be any suitable motor means, is attached at its forward end to a rearward end of the sampler housing by a quick release clamp 58. A piston rod (not shown) of the pneumatic cylinder connects to a rearward (leftward as shown) end of the plunger 46, such that the pneumatic cylinder can be actuated to reciprocate the plunger in both directions within the sampler housing bore.

Introduction of air to an air inlet 60 to the pneumatic cylinder 56 actuates the cylinder to extend the sampler plunger 46 forward in the sampler housing bore 28 to project the plunger and its recess 48 out of the forward end of the bore and into the vessel 40 to receive in the recess a sample of product of predetermined volume, as determined by the volume of the recess. Introduction of air to an air inlet 62 to the pneumatic cylinder then actuates the cylinder to retract the plunger 46 and its product sample carrying recess rearward into the sampler housing bore to move the recess and deliver the product sample in the recess to a sample collection point 64 in the bore. At the sample collection point, the product sample passes downward out of the plunger recess and out of the sampler 22 through a sample outlet port 66 in the sampler housing 26, into and through an outlet tube 68 and an outlet adapter 70 attached to the outlet tube by a quick connect clamp 72. To facilitate collection of a dry product sample in, and discharge of the dry product sample from, the plunger recess, the plunger may be extended forward in a jerky, jackhammer-like manner, to break up the product in the vessel and cause it to drop into the annular recess in the sampler plunger. It also is contemplated that the plunger may then be retracted in the same jackhammer-like manner to cause the sample to be discharged from the plunger recess at the sample collection point 64. Control over introduction of air to the inlets 60 and 62 to the pneumatic cylinder 56, in a manner to impart a jackhammer-like motion to the plunger, may be accomplished through use of a 4-way valve (not shown). To further facilitate removal of a product sample from the plunger recess, a port 74 extends through the sampler housing diametrically opposite from the sample collection point 64, through which a suitable fluid may be introduced, if necessary or desired, to move the product sample out of the plunger recess and through the sample outlet port 66.

It is desirable that isolation be maintained between the sample collection point 64 in the sampler 22 and the interior of the vessel 40, and the plunger seals 50 and 52 provide such isolation. The plunger seal 52 on the rearward side of the plunger recess 48 remains in the sampler housing bore 28 at all times during reciprocation of the plunger, and during forward extension of the plunger, the seal 52 forms a seal within the bore in front of the sample outlet port 66 before the forward plunger seal 50 moves out of the forward end 44 of the bore and into the vessel 40. During rearward retraction of the plunger, the forward plunger seal 50 enters the sampler housing bore before the rearward plunger seal 52 begins to move over and expose the sample outlet port. In this manner, a seal is at all times maintained between product in the vessel and the sample outlet port, so that only product samples received in the plunger recess 48 ever reach the outlet port 66. The seal 54 at the rearward end of the plunger blocks passage of any sampled product rearward to the pneumatic cylinder and passage of any pneumatic fluid forward to the sampler housing bore. With reciprocation of the plunger, the seal 54 also wipes clean the sampler housing bore between the rearward end of the bore and the sample outlet port. All of the seals serve the further purpose of supporting the plunger 46 in proper axial alignment within the sampler housing bore.

While product samples obtained by the sampler 22 can be analyzed one at a time, a common purpose of sampling is to obtain a representation of and track changes in the nature of product being generated over time. This is accomplished by obtaining and collecting, over time, a plurality of discrete product samples, and then admixing the samples before analysis to obtain a mixture that represents a composite of the product generated while the samples were obtained. Conventionally, samples are collected in a sample collection container which, upon becoming full, is replaced with an empty container, with the length of the interval between replacements being dependent upon the capacity of the container, the product-sampling rate and the volumetric size of each discrete product sample. It can happen that the need to replace sample collection containers occurs much more frequently than is convenient and desired. The invention overcomes this disadvantage, and the product sample collection station 24 is uniquely adapted to significantly extend the time interval between required replacements of full with empty sample collection containers.

Figure 2:
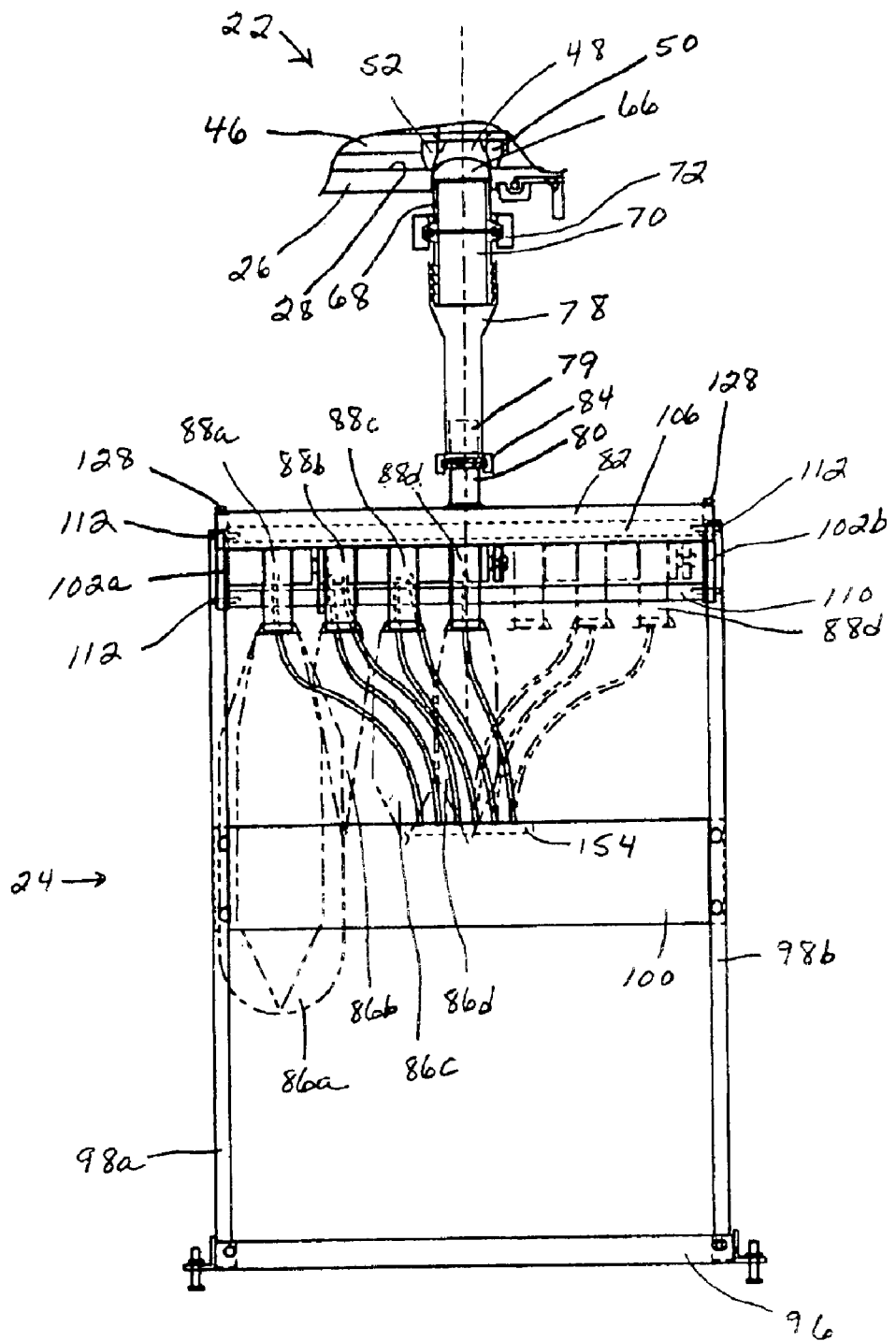
FIG. 2 is a partial front elevation view of the sampling apparatus.
Figure 3:
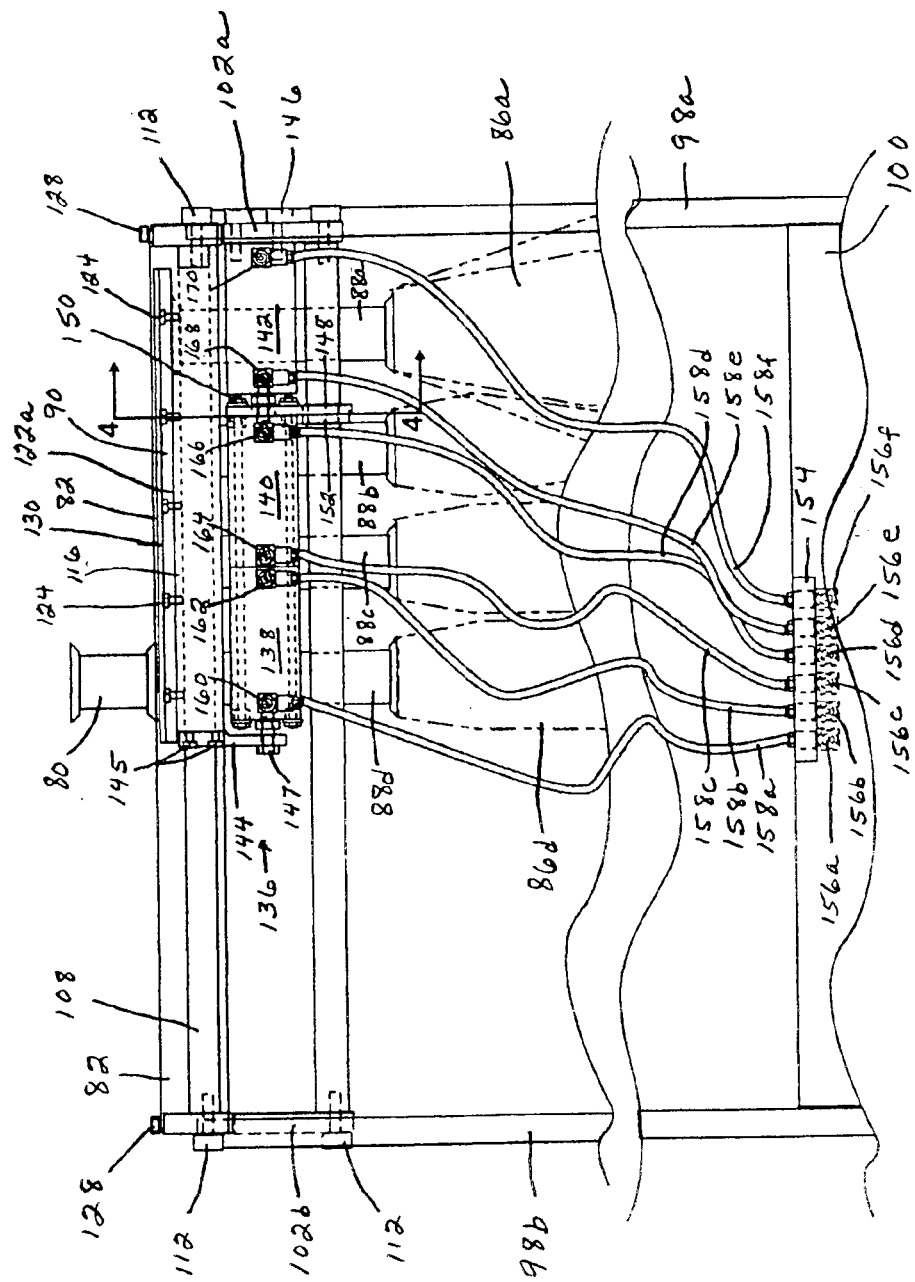
FIG. 3 is a partial back elevation view of the sample collection station.
Figure 4:
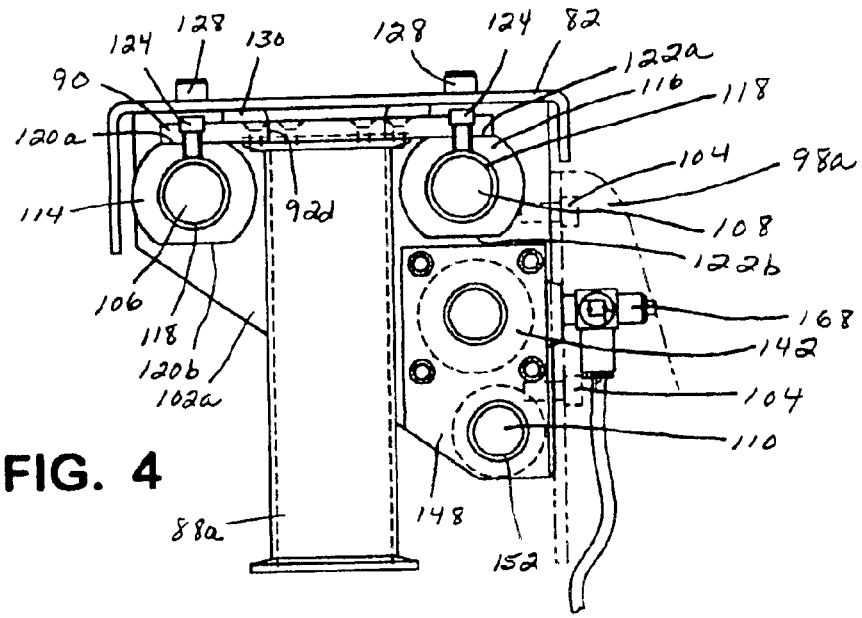
FIG. 4 is a side elevation view, taken generally along the lines 4—4 of FIG. 3, of an upper end of the sample collection station.

As seen in FIGS. 1 and 2, the sample collection station 24 is located vertically below the sampler 22. A conduit 78, which as shown is a flexible tube, but may be a rigid tube or pipe, extends between the sampler outlet adapter 70 and a stationary inlet adapter 79 coupled to a stationary inlet spout 80 of the sample collection station. The spout is carried on a stationary cover 82 in communication with a passage 83 through the cover and a lower end of the inlet adapter is connected to an upper end of the spout by a quick release clamp 84. The upper end of the flexible tube 78 may be pushed onto the sampler outlet adapter 70 and the lower end may be pushed onto the collection station inlet adapter 79, with the hose then providing a path through which product samples obtained by the sampler are gravitationally conveyed to the sample collection station.

Product samples delivered by the sampler 22 to the sample collection station 24 are directed into selected ones of a plurality of product sample collection containers 86*a*–*d*. The collection containers may be of the same or different capacities, and in the embodiment shown the collection container 86*a* is larger than the others. Each collection container 86*a*–*d* is supported around an upper inlet thereto by a lower outlet end of a respective one of a plurality of movable spouts 88*a*–*d*. An upper inlet end of each movable spout is connected to a lower side of a movable deck 90 around a respective one of a plurality of passages 92*a*–*d* formed through the deck. The plurality of deck passages 92*a*–*d*, and therefore the upper inlet ends to the plurality of movable spouts 88*a*–*d*, are in linearly aligned spaced relationship. Although as shown the spouts 88*a*–*d* are parallel and their lower outlet ends are in linearly aligned spaced relationship, they need not be, but instead the spouts can extend in non-parallel manners, if and as required, in order to accommodate attachment of various types of collection containers at their lower outlet ends. As will be described, the sample collection station 24 includes actuating means for linearly indexing or moving the deck 90 in both directions along the linear alignment of the deck passages 92*a*–*d*, relative to the stationary cover 82, to position selected ones of the deck passages beneath and into communication with the passage 83 through the cover. In this manner, product samples delivered by the sampler 22 through the tube 78 to the sample collection station 24 may be directed selected ones of the inlets to the sample collection containers 86*a*–*d*.

An advantage afforded by the sampling apparatus is to allow unattended collection of product samples for an extended time, such as for the duration of an eight-hour work shift. Thus, with four sample collection containers as shown, each may in turn be positioned to receive multiple discrete product samples continuously for two hours, after which the sample collection station may be operated to linearly index the movable deck 90 to position a different deck passage 92a–d into communication with the cover passage 83 to direct product samples into a fresh sample collection container 86a–d for the next two-hour period. This eliminates the need for a person to attend the sampler but once during an eight-hour work shift. Multiple sample containers, each utilized for a given period, also allow a determination of how product composition changes over time.

Another advantage afforded by the sampling apparatus resides in the linearly spaced alignment of the inlets to the sample collection containers. This places the sample collection containers themselves either in or at least generally in side-by-side relationship, with the desirable result that an operator has an unobstructed view of the containers and can simultaneously view all of the containers during a visual inspection of the sampling apparatus, since none of the containers will be blocked from view by others of the containers. In consequence, an operator is able to readily visually discern whether any of the containers are full and require replacement, or a problem exists, such as a blockage in the sample delivery paths to the containers.

The sample collection station 24 includes a frame 94 comprising a base 96, side legs 98a–b and a cross member 100 extending between the legs. End caps 102a–b attach to upper ends of respective legs 98a–b by fasteners 104, and three cylindrical rails 106, 108 and 110 extend between and are connected to facing sides of the end caps by fasteners 112 extending through the end caps and into longitudinal ends of the rails. The three rails are parallel, the upper rails 106 and 108 are generally at the same elevation, and the lower rail 110 is below the rail 108. Carriers 114 and 116, having axially extending longitudinal passages, are supported for sliding linear back and forth movement along respective ones of the rails 106 and 108 by bushings 118 in opposite longitudinal ends of the carrier passages. Each bushing extends inward into its associated carrier passage by a length equal to about one diameter of the rail along which the bushing and carrier slides.

The carrier 114 has diametrically opposed longitudinally extending upper and lower planar surfaces 120a–b and the carrier 116 has diametrically opposed longitudinally extending upper and lower planar surfaces 122a–b. The deck 90 is carried on and between the upper planar surfaces 120a and 122a of the carriers 114 and 116, and is attached to the carriers by fasteners 124 that extend through passages 126 in the deck and into the carriers. The deck is longer than the carriers in the longitudinal direction and opposite longitudinal ends of the deck extend beyond the longitudinal ends of the carriers. The carriers 114 and 116 support the deck 90 for linear back and forth movement along the rails 106 and 108.

Figure 7B:
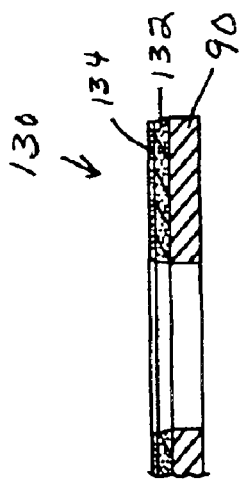
FIG. 7B is a partial cross-sectional view of the deck assembly, taken generally along the lines 7B—7B of FIG. 7A.
Figure 7A:
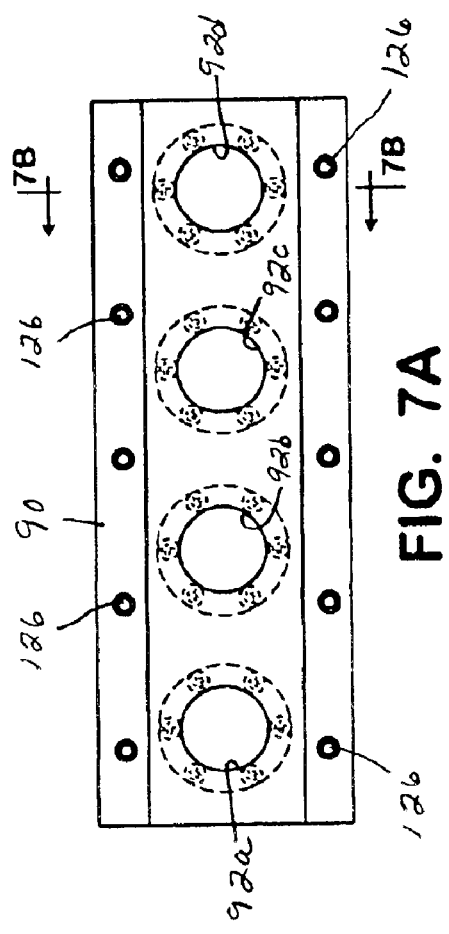
FIG. 7A is a top plan view of a deck assembly of the sample collection station.
Figure 7D:
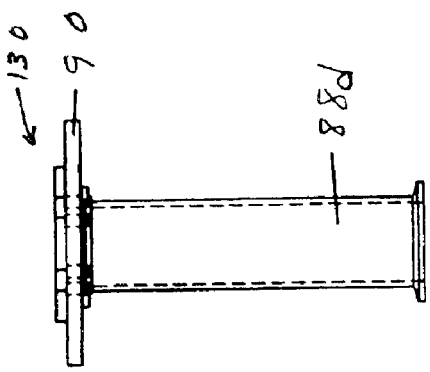
FIG. 7D is a side elevation view of the deck assembly, taken generally along the lines 7D—7D of FIG. 7C.
Figure 7C:
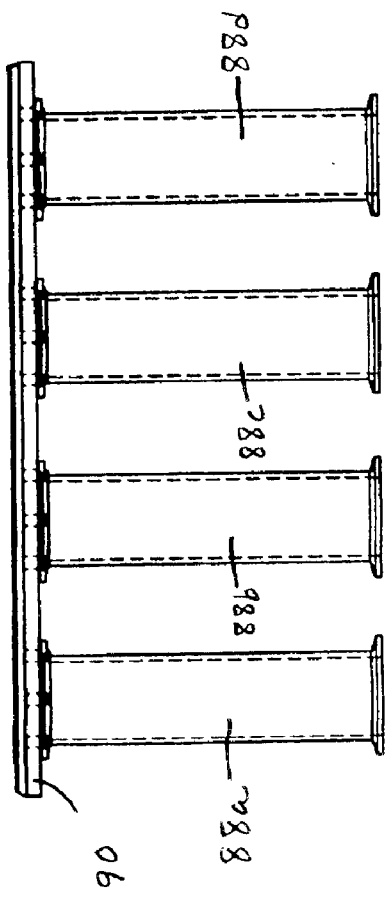
FIG. 7C is a front elevation view of the deck assembly.

The cover 82 extends between and is attached at opposite longitudinal ends to upper surfaces of the end caps 102a–b by fasteners 128. This positions the cover to extend longitudinally over and along the movable deck 90. In operation of the sample collection station 24, the deck is linearly indexed or moved in both directions along the linear alignment of the deck passages 92a–d, and relative to the stationary cover 82, to position selected ones of the deck passages beneath and into communication with the passage 83 through the cover. This indexing of the movable deck enables product samples obtained by the sampler 22 and delivered into and through the tube 78 to the fixed inlet spout of the sample collection station 24 to be directed through the cover passage 83 and into and through a selected one of the deck passages 92a–d and its associated spout 88a–d into an associated sample collection container 86a–d. It is desirable that product samples be maintained generally isolated from atmosphere while being delivered from the sampler to a selected one of the collection containers, both to prevent contamination of the samples by the atmosphere and contamination of the atmosphere by the samples. For the purpose, a seal means 130 is on the upper surface of the deck 90 and extends between the deck and the lower surface of the overlying cover 82. The seal means is best shown in FIG. 7B, and may comprise a sheet 132 of an adhesive foam that is adhered to and extends across the upper surface of the deck, along with a sheet 134 of a low friction bearing material that is adhered to and extends across an upper surface of the adhesive foam sheet. Passages are formed through the seal means 130 in axial alignment with and of the same diameter as the passages 92a–d through the deck, and the passages advantageously are tapered to have an increasing diameter in the upward direction to facilitate movement of product samples from the cover passage 83 into and through the seal means passages. The seal means 130 fills the space between the deck 90 and the cover 82 to provide a seal between the deck and cover, with the low friction bearing material sheet 134 facilitating longitudinal movement of the deck relative to the cover.

To linearly index the deck 90 relative to the cover 82 in order to align a selected one of the deck passages 92a–d with the cover passage 83, so that product samples are directed into an inlet to selected one of the sample collection containers 86a–d, the sample collection station 24 includes motor means for moving the deck. The motor means may be of any suitable type, such as electric or pneumatic motor means, and in the present embodiment comprises pneumatic motor means, indicated generally at 136.

A seen in FIGS. 3 and 5A–5D, for the situation where there are four sample collection containers 86a–d and four deck passages 92a–d, the motor means 136 may comprise three pneumatic cylinders 138, 140 and 142 that are selectively actuated to linearly index the deck 90 to move selected ones of the deck passages beneath and into communication with the cover passage 83. The pneumatic cylinders are connected longitudinally in series, along the longitudinal axes of their piston rods, between the end cap 102a and a driver 144 attached by fasteners 145 to an end of the carrier 116 toward the end cap 102b. The pneumatic cylinders are connected such that the closed end of the pneumatic cylinder 142 is attached to the end cap 102a by fasteners 146, and outer ends of the piston rods of the pneumatic cylinders 140 and 142 are connected together. In addition, the closed ends of the pneumatic cylinders 138 and 140 are joined, and the outer end of the piston rod of the pneumatic cylinder 138 is attached by a fastener 147 to the driver 144 to linearly move the driver and thereby the carrier 116 and deck 90. The rail 108 extends through a passage in the driver 144 and the driver, by virtue of its attachment to the carrier 116, supports and stabilizes the pneumatic cylinders 138, 140 and 142 in their horizontal, longitudinally aligned orientation. To further support and stabilize the pneumatic cylinders, a guide 148 is attached at its upper end by fasteners 150 to the closed end of the pneumatic cylinder 140, and at its lower end carries a bushing 152 through which the rail 110 extends for linear movement of the guide along the rail. The rail 110 supports the guide and the guide, in turn, provides additional support and stability to the pneumatic cylinders.

Means are provided for actuating the three pneumatic cylinders 138, 140 and 142 to four different states in order to linearly index the deck 90 and bring selected ones of the deck passages 92*a–d* into aligned communication with the cover passage 83, so that product samples delivered by the sampler 22 to the sample collection station 24 are directed into inlets to selected ones of the sample collection containers 86*a–d*. The means for actuating includes a manifold 154 having a plurality of inlets 156*a–f* coupled to a controller (not shown) that operates to introduce pressurized air simultaneously to a selected three of the inlets, while simultaneously venting the remaining three inlets to atmosphere. The inlets 156*a–f* are coupled through the manifold to respective ones of a plurality of air lines 158*a–f* that are in turn coupled to respective ones of a plurality of flow control valves of the pneumatic cylinders. The air lines 158*a–b* connect to respective flow control valves 160 and 162 of the pneumatic cylinder 138, the air lines 158*c–d* connect to respective flow control valves 164 and 166 of the pneumatic cylinder 140, and the air lines 158*e–f* connect to respective flow control valves 168 and 170 of the pneumatic cylinder 142. Air under pressure applied to the flow control valves 162, 164 and 170 actuates the respective pneumatic cylinders 138, 140 and 142 to extend their piston rods, while air under pressure applied to the flow control valves 160, 166 and 168 actuates the respective pneumatic cylinders 138, 140 and 142 to retract their piston rods. To better control movement of the piston rods of the pneumatic cylinders, the flow control valves allow a free flow of pressurized air into the pneumatic cylinders, and restrict a flow of air exhausting from the pneumatic cylinders.

Figure 5A:
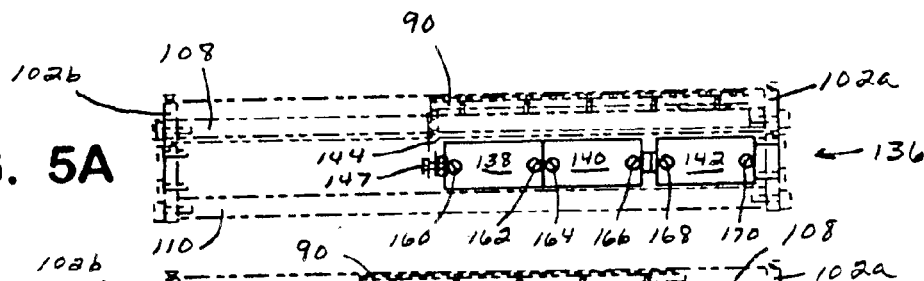
FIGS. 5A–5D illustrate the various actuated states of pneumatic cylinders that index the plurality of sample collection containers to place selected ones of the plurality into position to receive product samples delivered from the sampler.

FIGS. 5A–D show the four possible states of the pneumatic cylinders 138, 140 and 142 in their use to move selected ones of the deck passages 92*a–d* into aligned communication with the cover passage 83 in order to direct product samples delivered by the sampler 22 into inlets to selected ones of the sample collection containers 86*a–d*. As seen in FIG. 5A, with pressurized air applied to the flow control valves 160, 166 and 168 while the flow control valves 162, 164 and 170 are vented to atmosphere, the piston rods of all of the pneumatic cylinders 138, 140 and 142 are retracted. This linearly indexes the movable deck 90 to a position where the deck passage 92*d* is in aligned communication with the cover passage 83, so that product samples delivered by the sampler through the tube 78 and the stationary spout 80 are directed through the deck passage 92*d* and the spout 88*d* into the sample collection container 86*d*.

Figure 5B:
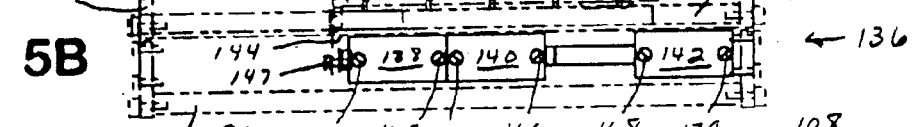

Upon the collection container 86*d* becoming full or when it is otherwise desired to direct product samples into another sample collection container, such as the container 86*c*, as seen in FIG. 5B, pressurized air is applied to the flow control valves 160, 166 and 170, and the flow control valves 162, 164 and 168 are vented to atmosphere. This causes the piston rods of the pneumatic cylinders 138 and 140 to be retracted and the piston rod of the pneumatic cylinder 142 to be extended, which linearly indexes the movable deck 90 to a position where the deck passage 92*c* is brought into aligned communication with the cover passage 83. Product samples delivered by the sampler 22 are then directed through the spout 88*c* into the sample collection container 86*c*.

Figure 5C:
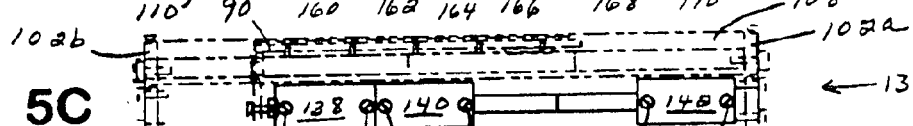

Should it be desired to next direct product samples into the sample collection container 86*b*, as seen in FIG. 5C, pressurized air is applied to the flow control valves 160, 164 and 170, while the flow control valves 162, 166 and 168 are vented to atmosphere. This retracts the piston rod of the pneumatic cylinder 138 and extends the piston rods of the pneumatic cylinders 140 and 142 to linearly index the deck 90 to a position where the deck passage 92*b* is in aligned communication with the cover passage 83. Product samples from the sampler 22 are then directed through the spout 88*b* into the sample collection container 86*b*.

Figure 5D:
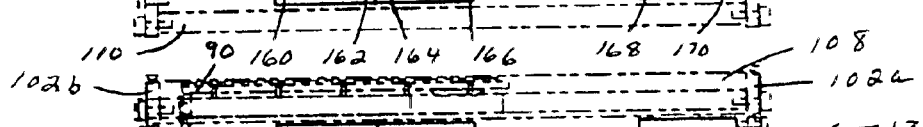

When product samples are to be directed into the sample collection container 86*a*, as seen in FIG. 5D, pressurized air is applied to the flow control valves 162, 164 and 170, while the flow control valves 160, 166 and 168 are vented to atmosphere. This extends the piston rods of all of the pneumatic cylinders 138, 140 and 142 to linearly index the deck 90 to a position where the deck passage 92*a* is in aligned communication with the cover passage 83, so that product samples then pass through the spout 88*a* into the sample collection container 86*a*.

Operation of the pneumatic cylinders 138, 140 and 142 to index the movable deck 90 of the sample collection station 24 to deliver product samples to selected sample collection containers 86*a–d* can be implemented either manually or automatically. For example, if samples are to be collected over an eight hour work shift, then for the case where the sample collection station has four sample collection containers, the sample collection station can either be manually indexed every two hours or it can be automatically indexed under control of a timer.

In use of the sampling apparatus to obtain samples of a dry powder product such as cocoa, the sample collection station 24 normally would be vertically below the sampler 22, for example it could rest on a floor, so that product samples obtained by the sampler are gravitationally delivered to the collection station. The flexible tube 78 can conveniently be used to convey product samples from the sampler to the collection station, but it is not necessary that the tube be flexible. Because the sampler outlet tube 68 and its outlet adapter 70 remain stationary during operation of the sampler 22, and because the sample collection station inlet spout 80 and its inlet adapter 79 also remain stationary during operation of the sample collection station 24, a rigid tube or pipe can, if desired or required, be used in place of the flexible tube 78 between the sampler outlet adapter and the sample collection station inlet adapter.

Should the sampler 22 require separation from the vessel 40 for repair or replacement, the quick release clamp 34 need simply be removed to allow withdrawal of the sampler housing 26 from the adapter 32, whereupon escape of product from the vessel can be prevented by closing the opening to the adapter with a cap 172 that is conveniently attached to the sampler by a tether 174.

While one embodiment of the invention has been described in detail, various modifications and other embodiments thereof may be devised by one skilled in the art without departing from the spirit and scope of the invention, as defined in the appended claims.

What is claimed is:

1. A sampling apparatus, comprising a sample collection station having a stationary inlet for receiving discrete samples, a plurality of sample collection containers, inlets to respective ones of said sample collection containers, said inlets being in linearly aligned spaced relationship, and means for indexing said inlets to said sample collection containers in both directions along said linear alignment of said inlets to move selected ones of said inlets into communication with said stationary inlet, so that discrete samples received at said stationary inlet are directed into selected ones of said sample collection containers.

2. A sampling apparatus as in claim 1, wherein said sample collection station further comprises a deck having passages therethrough in linearly aligned spaced relationship, said inlets to said sample collection containers are in communication with associated ones of said deck passages, and said means for indexing moves said deck to move said deck passages in both directions along said linear alignment of said deck passages to place selected ones of said deck passages into communication with said stationary inlet, so that discrete samples received at said stationary inlet are directed through selected ones of said deck passages into associated ones of said sample collection containers.

3. A sampling apparatus as in claim 2, wherein said inlets to said sample collection containers include a plurality of movable spouts carried by said deck and having inlets in communication with associated ones of said deck passages and outlets in communication with associated ones of said sample collection containers, whereby samples received at said stationary inlet are delivered through selected ones of said deck passages and associated spouts into associated sample collection containers.

4. A sampling apparatus as in claim 2, wherein said inlets to said sample collection containers comprise openings to said sample collection containers.

5. A sampling apparatus as in claim 2, wherein said means for indexing includes pneumatic motor means and said pneumatic motor means comprises plurality of pneumatic cylinders each having a cylinder and a piston rod and each being actuable between a first state where its piston rod is extended from its cylinder and a second state where its piston rod is retracted into its cylinder.

6. A sampling apparatus as in claim 5, wherein each said pneumatic cylinder has a longitudinal axis extending along a longitudinal axis of its piston rod, said plurality of pneumatic cylinders are connected in series along their longitudinal axes, and said plurality of series connected pneumatic cylinders are coupled to said deck and are individually selectively actuable between said first and second states to linearly move said deck in both directions along said linear alignment of said deck passages to position selected ones of said deck passages into communication with said stationary inlet.

7. A sampling apparatus as in claim 6, wherein said sample collection station includes a frame for supporting said stationary inlet, said deck, said sample collection containers and said plurality of pneumatic cylinders, said plurality of pneumatic cylinders is one less in number than the number of deck passages, and said series connected pneumatic cylinders are coupled at one longitudinal end to said frame and at an opposite longitudinal end to said deck for linearly moving said deck relative to said frame.

8. A sampling apparatus as in claim 1, further including a sampler for obtaining discrete samples and for delivering the samples to said sample collection station stationary inlet.

9. A sampling apparatus as in claim 1, wherein said sampler is vertically above said sample collection station, and including conduit means coupled between an outlet from said sampler and said stationary inlet of said sample receiving station for gravitationally conveying samples from said sampler outlet to said stationary inlet.

10. A sampling apparatus as in claim 9, wherein said sampler is for being coupled to a vessel containing product to be sampled and includes a plunger having a sample receiving recess that is extendable through an opening in the vessel and into the product in the vessel to receive in said plunger recess a sample of product, and that is then retractable from the vessel into a body of said sampler to deliver the product sample in said recess to said sampler outlet for movement of the product sample from said plunger recess and through said sampler outlet into said conduit for being gravitationally conveyed to said stationary inlet of said sample collection station.

11. A sampling apparatus, comprising a sampler for obtaining discrete samples of product and for providing the discrete product samples at an outlet from said sampler; and a sample collection station for receiving and collecting a plurality of said discrete product samples, said sample collection station having a stationary inlet for receiving discrete product samples from said sampler outlet, a plurality of sample collection containers, inlets to respective ones of said sample collection containers, said inlets being in linearly aligned spaced relationship, and means for indexing said inlets to said sample collection containers in both directions along said linear alignment of said inlets to move selected ones of said inlets into communication with said stationary inlet, so that discrete product samples received at said stationary inlet are directed into selected ones of said sample collection containers.

12. A sampling apparatus as in claim 11, wherein said sample collection station further comprises a deck having passages therethrough in linearly aligned spaced relationship, said inlets to said sample collection containers are in communication with associated ones of said deck passages, and said means for indexing moves said deck to move said deck passages in both directions along said linear alignment of said deck passages to place selected ones of said deck passages into communication with said stationary inlet, so that discrete product samples received at said stationary inlet are directed through selected ones of said deck passages into associated ones of said sample collection containers.

13. A sampling apparatus as in claim 12, wherein said inlets to said sample collection containers include a plurality of spouts carried by said deck and having inlets in communication with associated ones of said deck passages and outlets in communication with associated ones of said collection containers, whereby product samples received at said stationary inlet are delivered through selected ones of said deck passages and associated spouts into associated sample collection containers.

14. A sampling apparatus as in claim 13, wherein said sample collection station further includes a cover overlying said deck, said cover has a passage therethrough in communication with said stationary inlet, said means for indexing moves said deck to place selected ones of said deck passages into communication with said cover passage, and including means for sealing said cover to said deck around said cover passage and said deck passages.

15. A sampling apparatus as in claim 11, wherein said inlets to said sample collection containers comprise openings to said sample collection containers.

16. A sampling apparatus as in claim 12, wherein said means for indexing comprises pneumatic motor means including a plurality of pneumatic cylinders each having a cylinder and a piston rod and each being actuable between a first state where its piston rod is extended from its cylinder and a second state where its piston rod is retracted into its cylinder, and wherein each said pneumatic cylinder has a longitudinal axis extending along a longitudinal axis of its piston rod, said plurality of pneumatic cylinders are connected in series along their longitudinal axes, and said plurality of series connected pneumatic cylinders are coupled to said deck and are individually selectively actuable between said first and second states to linearly move said deck in both directions along said linear alignment of said deck passages to position selected ones of said deck passages into communication with said stationary inlet.

17. A sampling apparatus as in claim 11, wherein said sampler is vertically above said sample collection station, and including conduit means coupled between said sampler outlet and said sample collection station stationary inlet for conveying product samples from said sampler outlet to said collection station stationary inlet.

18. A sampling apparatus as in claim 17, wherein said sampler is for being coupled to a vessel containing product to be sampled and includes a plunger having a product sample receiving recess that is extendable through an opening to the vessel and into the product in the vessel to receive in said plunger recess a sample of product, and that is then retractable from the vessel into a body of said sampler to deliver the product sample in said recess to said sampler outlet for movement of the product sample from said plunger recess and through said sampler outlet into said conduit for being gravitationally conveyed to said stationary inlet of said sample collection station.

19. A sampling apparatus as in claim 18, wherein said conduit comprises a flexible tube.

20. A method of sampling product, comprising the steps of obtaining discrete samples of product; conveying discrete samples of product to a stationary sample receiving inlet; providing a plurality of sample collection containers; providing a corresponding plurality of inlets to the sample collection containers; linearly aligning the inlets in spaced relationship; and indexing the inlets in both directions along the linear alignment of the inlets to place selected ones of the inlets into communication with the stationary inlet, so that discrete product samples conveyed to the stationary inlet are directed into selected ones of the sample collection containers.

* * * * *